(12) United States Patent
Yacoub et al.

(10) Patent No.: US 9,874,509 B2
(45) Date of Patent: Jan. 23, 2018

(54) PARTICLE SENSOR, EXHAUST SYSTEM AND METHOD FOR DETERMINING PARTICLES IN THE EXHAUST GAS

(71) Applicant: Ford Global Technologies, LLC, Dearborn, MI (US)

(72) Inventors: Yasser Mohamed Sayed Yacoub, Cologne (DE); Matthew Allen Schneider, Aachen (DE)

(73) Assignee: Ford Global Technologies, LLC, Dearborn, MI (US)

( * ) Notice: Subject to any disclaimer, the term of this patent is extended or adjusted under 35 U.S.C. 154(b) by 273 days.

(21) Appl. No.: 14/724,049

(22) Filed: May 28, 2015

(65) Prior Publication Data
US 2015/0260630 A1 Sep. 17, 2015

Related U.S. Application Data

(62) Division of application No. 13/351,684, filed on Jan. 17, 2012, now Pat. No. 9,052,259.

(30) Foreign Application Priority Data

Jan. 20, 2011 (DE) ........................ 10 2011 002 936

(51) Int. Cl.
*G01M 15/10* (2006.01)
*G01N 15/06* (2006.01)
(Continued)

(52) U.S. Cl.
CPC ..... *G01N 15/0656* (2013.01); *G01N 15/0272* (2013.01); *G01N 15/08* (2013.01); *G01N 2015/084* (2013.01)

(58) Field of Classification Search
USPC .......................... 73/114.69, 114.71
See application file for complete search history.

(56) References Cited

U.S. PATENT DOCUMENTS 4,228,128 A * 10/1980 Esper .................... G01N 27/12
324/71.5
4,597,850 A * 7/1986 Takahasi ............ G01N 27/4077
204/426

(Continued)

FOREIGN PATENT DOCUMENTS

| CN | 101608564 A | 12/2009 |
| DE | 102008041809 A1 | 3/2010 |

(Continued)

OTHER PUBLICATIONS

Cheng, Xiao-bei et al., "Characteristics of Diesel Particle Size Distribution of Direct Injection Diesel Engine," Journal of Combustion Science and Technology, vol. 12, No. 4, pp. 335-339, Aug. 2006, 5 pages.

(Continued)

*Primary Examiner* — Eric S McCall
(74) *Attorney, Agent, or Firm* — Julia Voutyras; McCoy Russell LLP

(57) ABSTRACT

Embodiments of a particle sensor are provided. In one example, a particle sensor for an exhaust system comprises at least two inlet openings for an exhaust-gas flow of the exhaust system, wherein the inlet openings are of different sizes, and at least two sensor elements, wherein in each case one sensor element is arranged downstream of one inlet opening. In this way, the relative proportion of different-sized particles within the exhaust-gas flow may be determined.

13 Claims, 3 Drawing Sheets

(51) Int. Cl.
*G01N 15/02* (2006.01)
*G01N 15/08* (2006.01)

(56) References Cited

U.S. PATENT DOCUMENTS

| | | | |
|---|---|---|---|
| 5,171,335 A * | 12/1992 | Kojima | F01N 3/0211 |
| | | | 55/523 |
| 6,301,887 B1 | 10/2001 | Gorel et al. | |
| 7,055,495 B2 | 6/2006 | Yamaoka et al. | |
| 7,998,417 B2 * | 8/2011 | Hall | G01N 15/0656 |
| | | | 422/83 |
| 8,528,329 B2 | 9/2013 | Gibble et al. | |
| 2003/0074893 A1 | 4/2003 | Webb et al. | |
| 2004/0031262 A1 | 2/2004 | Gui et al. | |
| 2004/0103860 A1 | 6/2004 | zur Loye et al. | |
| 2004/0154581 A1 | 8/2004 | Yamaoka et al. | |
| 2004/0177830 A1 | 9/2004 | Yamaoka et al. | |
| 2005/0178111 A1 | 8/2005 | Kammel et al. | |
| 2005/0241302 A1 | 11/2005 | Weber et al. | |
| 2006/0289308 A1 * | 12/2006 | Shaddock | F01N 13/08 |
| | | | 204/424 |
| 2007/0068149 A1 | 3/2007 | Weber et al. | |
| 2008/0204749 A1 | 8/2008 | Haddock et al. | |
| 2008/0264036 A1 | 10/2008 | Bellovary | |
| 2009/0094963 A1 | 4/2009 | Mizoguchi et al. | |
| 2009/0258383 A1 | 10/2009 | Kovac et al. | |
| 2010/0236925 A1 * | 9/2010 | Uchikawa | C04B 38/02 |
| | | | 204/424 |
| 2011/0167802 A1 * | 7/2011 | Bruck | F02D 41/029 |
| | | | 60/274 |
| 2012/0006006 A1 * | 1/2012 | Hertzberg | F01N 3/021 |
| | | | 60/274 |
| 2012/0227389 A1 | 9/2012 | Hinderks | |
| 2013/0219990 A1 * | 8/2013 | Allmendinger | G01N 33/0027 |
| | | | 73/23.31 |
| 2013/0243659 A1 * | 9/2013 | Sutton | B01D 53/944 |
| | | | 422/168 |
| 2014/0042025 A1 * | 2/2014 | Furuta | G01N 27/4076 |
| | | | 204/427 |
| 2014/0223887 A1 * | 8/2014 | Duault | F01N 9/002 |
| | | | 60/274 |
| 2015/0102822 A1 * | 4/2015 | Okuda | G01N 27/62 |
| | | | 324/464 |
| 2016/0103055 A1 * | 4/2016 | Gaertner | F01N 11/00 |
| | | | 73/23.31 |

FOREIGN PATENT DOCUMENTS

| | | |
|---|---|---|
| EP | 1873511 A2 | 1/2008 |
| JP | 2006258071 A | 9/2006 |

OTHER PUBLICATIONS

Lu, Xiao-ming et al., "Experimental Study on Particle Size Distributions of an Engine Fueled with Blends of Biodiesel," Environmental Science, vol. 28, No. 4, pp. 701-705, Apr. 2007, 5 pages.

Lui, W. et al., "Characteristics of ultrafine particle from a compression-ignition engine fueled with low sulfur diesel," ,Chinese Sci Bull, vol. 54, No. 12, pp. 1773-1778, Jun. 2009, (with partial translation), 7 pages.

Partial Translation of Office Action of Chinese Application No. 2012100176300, Issued Dec. 8, 2015, State Intellectual Property Office of PRC, 31 pages.

Anonymous, "Dual Path Purge Monitor Using Hydrocarbon Sensor to Diagnose Boosted EVAP Purge Path," IPCOM No. 000237283, Published Jun. 11, 2014, 2 pages.

Anonymous, "A Carbon Canister With Internal Hydrocarbon Sensors to Measure Loading," IPCOM No. 000240421, Published Jan. 29, 2015, 2 pages.

Partial Translation of Office Action of Chinese Application No. 201210017630.0, dated Apr. 1, 2015, State Intellectual Property Office of PRC, 8 pages.

* cited by examiner

PARTICLE SENSOR, EXHAUST SYSTEM AND METHOD FOR DETERMINING PARTICLES IN THE EXHAUST GAS

CROSS REFERENCE TO RELATED APPLICATIONS

The present application is a divisional of U.S. patent application Ser. No. 13/351,684, entitled "PARTICLE SENSOR, EXHAUST SYSTEM AND METHOD FOR DETERMINING PARTICLES IN THE EXHAUST GAS," filed on Jan. 17, 2012, which claims priority to German Patent Application No. 102011002936.2 filed on Jan. 20, 2011, the entire contents of each of which are hereby incorporated by reference for all purposes.

FIELD

The disclosure relates to a particle sensor in an exhaust system.

BACKGROUND AND SUMMARY

To reduce the particle emissions of a diesel engine, use is made of soot particle filters. For example, to monitor the effectiveness of said filters, sensors are used which measure the particle content of the exhaust gases flowing through the filter.

At present, resistance particle sensors are known in which two or more metallic electrodes are formed, wherein the particles, in particular soot particles, that are accumulated cause the electrodes, which engage into one another in a comb-like manner, to be short-circuited, and therefore, with increasing particle concentration on the sensor surface, a decreasing resistance or a decreasing impedance (or an increasing current if a constant voltage is applied) can be measured between the electrodes. The measured current or the change thereof can be correlated with the accumulated mass of particles and therefore also with the particle concentration prevailing in the exhaust gas.

Sensors or systems of said type are known for example from DE102008041809A1 and EP1873511A2/A3.

In general, the particle or solid body sensor may be used in the exhaust system to detect solid and also soluble fractions in the exhaust-gas flow. For this purpose, use is conventionally made of a resistance element whose resistance varies when substances from the exhaust gas precipitate on the sensor element. This requires regular regeneration of the sensor by periodically increasing the temperature of the sensor element in order to evaporate the accumulated material. The derivative of the sensor signal with respect to time may be used to calculate the mass throughflow of the solid or soluble materials in the exhaust gas. However, the size of the particles within the exhaust flow cannot be determined with this conventional type of sensor.

The inventors herein have recognized the issues with the above approach and offer a particle sensor to at least partly address them. In one embodiment, a particle sensor for an exhaust system comprises at least two inlet openings for an exhaust-gas flow of the exhaust system, wherein the at least two inlet openings are of different sizes, and at least two sensor elements, wherein in each case one sensor element is arranged downstream of one inlet opening.

In this way, the relative portion of different sized particles within the exhaust may be determined. In some examples, the distribution of particle sizes within the exhaust may be monitored, and a change in the distribution that exceeds a threshold may indicate a degraded combustion condition, which may be mitigated by adjusting one or more engine operating parameters.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
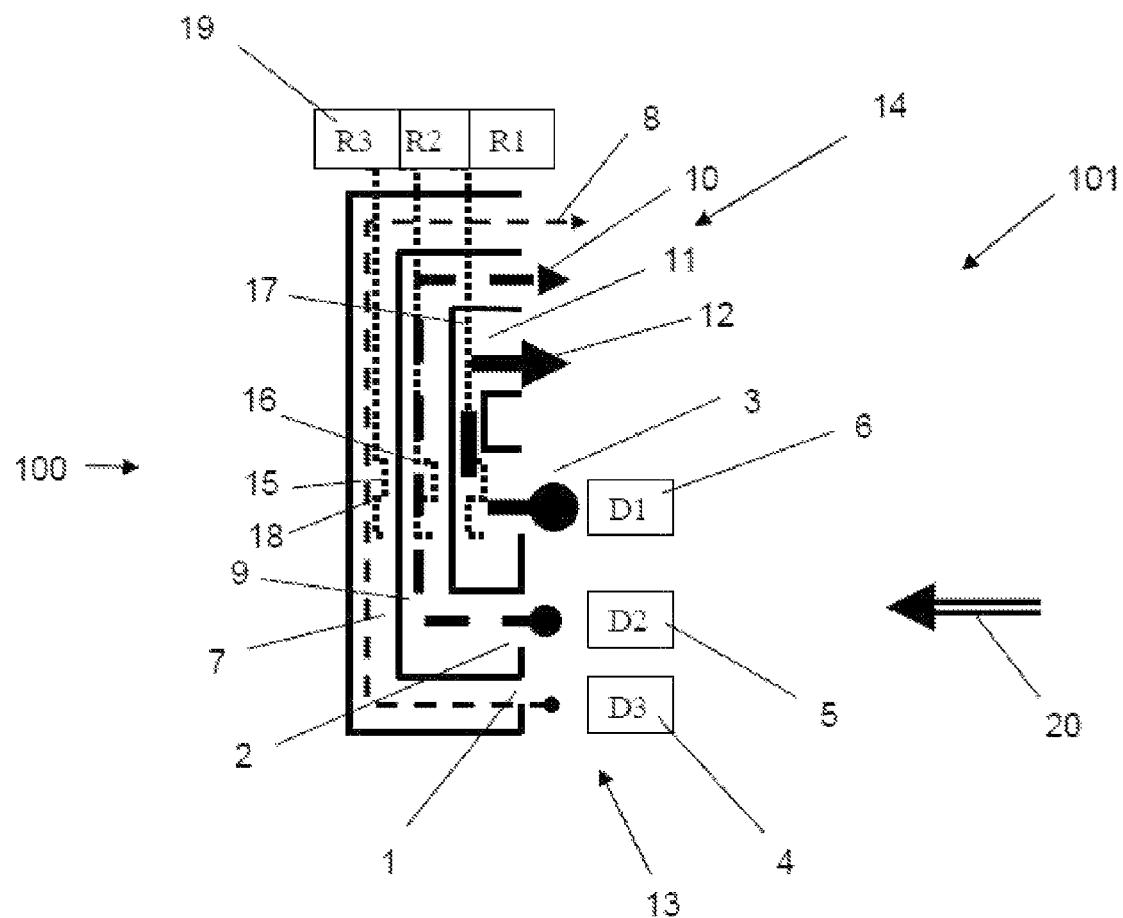
FIG. 1 shows a schematic illustration of a particle sensor according to the disclosure.

According to a first aspect of the disclosure, a particle sensor for an exhaust system comprises at least two inlet openings for an exhaust-gas flow of the exhaust system, wherein the inlet openings are of different sizes, and at least two sensor elements, wherein in each case one sensor element is arranged downstream of one inlet opening.

The particle sensor permits an improved measurement of the particles in the exhaust gas, because it is now possible for measurement to be carried out in a manner differentiated by particle size. It is thus possible for certain particle sizes and also a size distribution to be identified and examined. The specific resistance of a particle sensor with regard to the accumulated particles is also dependent on the size of the particles. The size of the particles which pass to the sensor element is determined by the size and/or shape of the inlet openings. The inlet openings act as a screen or a filter for sorting the particles.

The sensor element may have a resistance element. This is the generally used sensor type, which has the advantage of good integration in existing systems.

The sensor element may be arranged in a duct adjoining the inlet opening. Said duct or chamber conducts the exhaust-gas flow to the sensor element and may be adapted to the respective sensor element and/or to the particle size or the size of the inlet opening.

The size of at least one inlet opening may be variable. For example, the size may be varied by an actuating element in order to adapt the measurement to certain situations or specific particle sizes. Said variation may also be carried out during ongoing operation, for example in a manner controlled by a control processor of the exhaust-gas aftertreatment system.

The integral mass of particles of a size smaller than or the same as a smallest inlet opening may be a function of the sensor element arranged downstream of the smallest inlet opening. The smallest particles are correspondingly measured only behind, or in other words downstream, of the smallest inlet opening. The smallest particles also pass through the larger openings to further sensor elements, but are not taken into consideration there. The measurement at only one sensor element is the simplest implementation.

The integral mass of particles of a size smaller than or the same as a next-larger inlet opening than the smallest inlet opening and larger than the smallest inlet opening may be a function of the sensor element arranged downstream of the next-larger inlet opening minus the function of the sensor element arranged downstream of the smallest inlet opening. For the next-larger particles, the sensor element arranged downstream of the next-larger inlet opening is used. To eliminate the fraction of the smallest particles, the function of the smallest particles is subtracted. The integral mass, that is to say the particles deposited within a certain time period, of the next-larger particles can thus be determined. An analogous procedure is followed for further inlet openings and sensor elements for larger particles and/or intermediate sizes of particles.

According to a second aspect of the disclosure, an exhaust system of an internal combustion engine for a motor vehicle comprises a particle sensor as described above. The same advantages and modifications as described above apply.

According to a further aspect of the disclosure, a method for determining particles in the exhaust gas of an internal combustion engine comprises measuring particles of a first size downstream of a first opening of a first size, and measuring particles of a second size downstream of a second opening of a second size.

The same advantages and modifications as described above apply. The openings filter or organize the particles according to their size; in the process, the exhaust-gas flow is split up. The particles are subsequently measured in the split-up exhaust-gas flows, such that statements can be made regarding the occurrence according to size and with regard to the size distribution.

Particles of further sizes may be measured. For example, three particle sizes may be measured downstream of three openings or inlet openings. A precise measurement of the size distribution in the exhaust-gas flow can thus also be carried out.

The particles may be measured by a sensor element, in particular a resistance element. This is the generally routine approach, which offers good compatibility and a broad range of uses.

The number and size of the openings may be determined by the soot distribution in the exhaust gas. In this way, the particle sensor may be adapted to the expected composition of the exhaust-gas flow and thus optimally set for the respective engine and/or the exhaust-gas aftertreatment system. Alternatively, it is also possible to use other characteristics of the exhaust gas for the definition of the particle sensor, such as for example the distribution of solid particles or of fine dust.

The size of at least one opening can be varied. This increases flexibility during operation, because an adaptation and therefore adjustment of the measurement range is possible even after the installation of the particle sensor.

The size of an opening may be varied in order to examine a certain particle size. This is a targeted setting of the particle sensor to a certain measurement size.

The size of an opening may be varied in conjunction with a cleaning of a sensor element arranged downstream of the opening. During a cleaning or regeneration of the accumulated particles, the sensor element may, in the case of soot particles, be heated by electric heating to temperatures of over 550 to 600° C., as a result of which the particles are evaporated.

The drawings serve merely for the explanation of the disclosure, and do not restrict the disclosure. The drawings and the individual parts are not necessarily drawn to scale. The same reference symbols are used to denote identical or similar parts.

FIG. 1 shows a particle sensor 100 for measuring particles in an exhaust-gas flow 20 of an internal combustion engine for example of a motor vehicle. The particle sensor 100 is a constituent part of an exhaust system 101 or is arranged in an exhaust system 101. Particles such as for example soot particles of different sizes are present in the exhaust-gas flow 20.

Aside from merely detecting the amount of particles in the exhaust-gas flow, the particle sensor 100 can also detect a size distribution of the particles.

For this purpose, the particle sensor 100 has three inlet openings 1, 2 and 3. The inlet openings are of different sizes, wherein the inlet opening 1 is the smallest inlet opening, the inlet opening 2 is a mid-sized inlet opening, and the inlet opening 3 is the largest inlet opening. The inlet openings 1, 2 and 3 act as a filter or a screen which assigns the particles to the respective inlet opening as a function of their size.

Illustrated by way of example are three size distributions D3 4, D2 5 and D1 6. The size distribution 6 encompasses particles with the largest circumference or diameter. The particles of size distribution 6 or D1 can pass only through the largest inlet opening 3 but cannot pass through the smaller inlet openings 1 or 2. The particles of size distribution 5 or D2 can pass through the largest inlet opening 3 and the mid-sized inlet opening 2 but cannot pass through the smallest inlet opening 1. The particles of size distribution 4 or D3 can pass through all three inlet openings 1, 2 and 3.

The inlet opening 1 is adjoined by a duct 7 through which the smallest particles, that is to say the particles of the size distribution D3, flow in the direction of the arrow 8. The inlet opening 2 is adjoined by a duct 9 through which the smallest and mid-sized particles, that is to say the particles of the size distributions D2 and D3, flow in the direction of the arrow 10. The inlet opening 3 is adjoined by a duct 11 through which the smallest, mid-sized and largest particles, that is to say the particles of the size distributions D1, D2 and D3, flow in the direction of the arrow 12. The three inlet openings 1, 2 and 3 form an inlet side 13 of the particle sensor 100. The exhaust-gas flow 2 emerges from the particle sensor 100 again at an outlet side 14 of the particle sensor 100.

A first sensor element 15 is arranged in the first duct 7. Correspondingly, a second sensor element 16 is arranged in the second duct 9. A third sensor element 17 is arranged in the third duct 11.

Each sensor element 15, 16 and 17 comprises a resistance element 18 which is connected to an evaluation unit 19. For the sake of clarity, only the sensor element 15 has been provided with the reference numerals for the resistance element and the evaluation unit. The evaluation unit 19 may be a constituent part of the sensor element, of the particle sensor 100 and/or of a controller, such as for example a controller of the exhaust-gas aftertreatment system.

It is also possible for two or more than three size distributions and, correspondingly, inlet openings, ducts and sensor elements to be taken into consideration or used. The number is determined in accordance with the desired measurement resolution and/or the characteristics of the engine or of the exhaust-gas aftertreatment system.

In the example shown in FIG. 1, three size distributions D1, D2 and D3 are measured by virtue of the accumulated particles, in this case for example soot particles, being measured using three sensor elements 15, 16 and 17 (R1, R2 and R3). The size of the particles entering in each case is controlled by the size of the respective inlet opening 1, 2 and 3.

The integral mass of the respective sizes is calculated or measured by measuring the variation of the respective sensor element 15, 16 and 17 or of the associated resistance element 18.

In detail, the integral masses are determined as follows:

The integral mass of particles of a size D smaller than or equal to D3 is measured as a function of the sensor element 15 (Func(R3)).

The integral mass of particles of a size D larger than D3 and smaller than or equal to D2 is measured as a function of the sensor element 16 minus the function of the sensor element 15 (Func(R2)−Func(R3)). The subtraction of the function of the sensor element 15 serves for the correction of the measurement values. The effects caused by the particles of size D smaller than or equal to D3 are thus eliminated.

The integral mass of particles of a size D larger than D2 and smaller than or equal to D1 is measured as a function of the sensor element 17 minus the function of the sensor element 16 and minus the function of the sensor element 15 (Func(R1)−Func(R2)−Func(R3)). The subtraction of the functions of the sensor elements 16 and 15 serves for the correction of the measurement values. The effects caused by the particles of size D smaller than or equal to D2 are thus eliminated.

The number and size of the inlet openings or of the sensor elements may be selected on the basis of the required soot distribution, in order thereby to have an optimum measurement and monitoring in the relevant size ranges. The calculation for more than three particle size distributions takes place analogously to the determination described above.

Furthermore, one or more inlet openings may be of variable size. The inlet size may be varied by means of a controlled actuation. It is thus possible for a certain size distribution of interest to be set and measured. Measurements with a varying opening size may also be carried out in temporal succession. The measurement resolution can thus be increased by means of temporal extension. The measurement resolution can be correspondingly adapted by means of the number of individual measurement paths (inlet opening, sensor element) or by means of one or more variable inlet openings with temporally staggered measurements.

Said measurements may for example be carried out between cleaning processes of the sensor elements.

Figure 2:
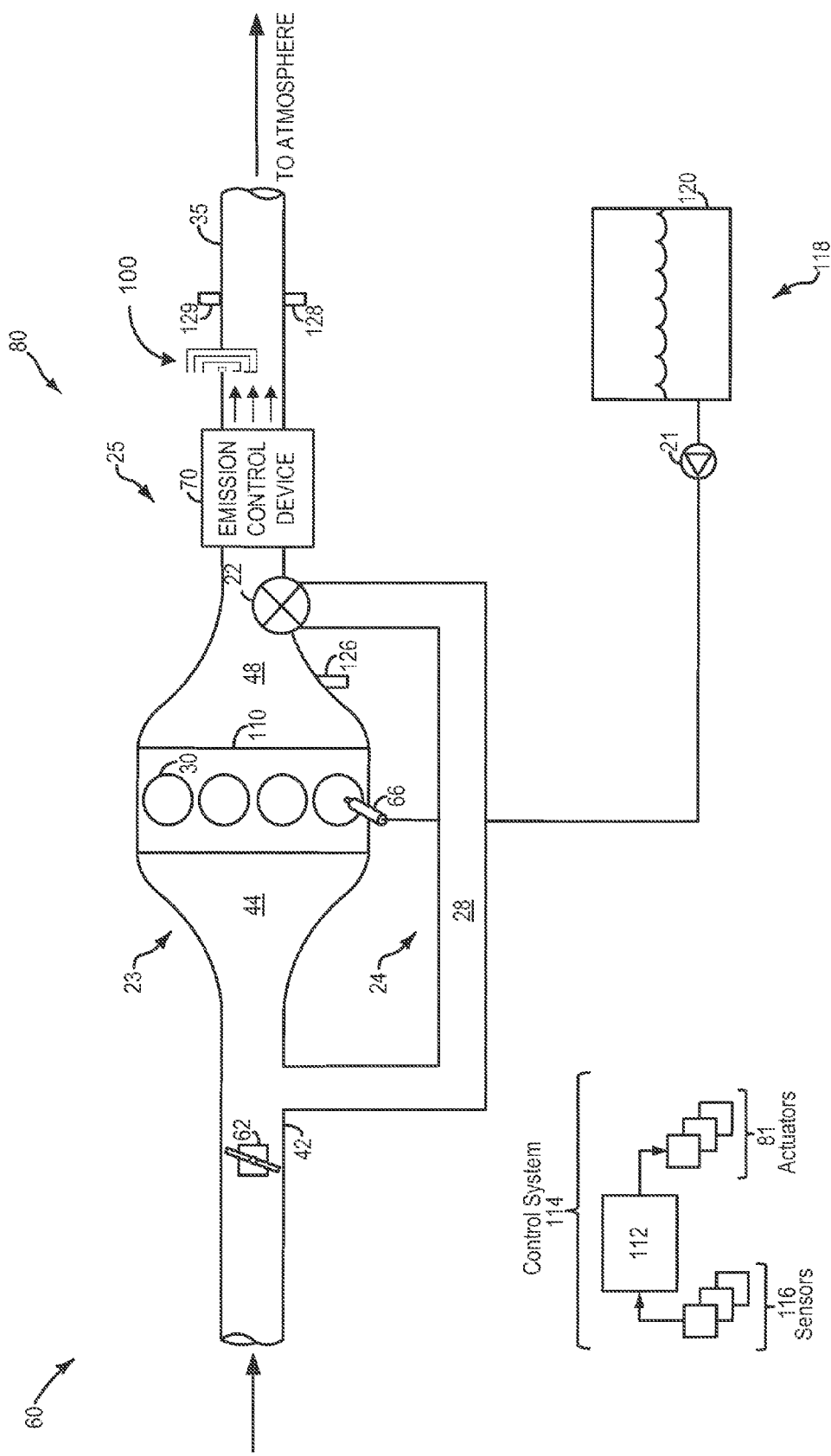
FIG. 2 shows the particle sensor of FIG. 1 arranged in a vehicle system.

FIG. 2 shows a schematic depiction of a vehicle system 60. The vehicle system 60 includes an engine system 80 coupled to a fuel system 118. The engine system 80 may include an engine 110 having a plurality of cylinders 30. The engine 110 includes an engine intake 23 and an engine exhaust system 101. The engine intake 23 includes a throttle 62 fluidly coupled to the engine intake manifold 44 via an intake passage 42. The engine exhaust 101 includes an exhaust manifold 48 leading to an exhaust passage 35 that routes exhaust gas to the atmosphere. The engine exhaust 25 may include one or more emission control devices 70, which may be mounted in a close-coupled position in the exhaust. One or more emission control devices may include a three-way catalyst, lean NOx trap, diesel particulate filter, oxidation catalyst, etc. It will be appreciated that other components may be included in the engine such as a variety of valves and sensors.

Fuel system 118 may include a fuel tank 120 coupled to a fuel pump system 21. The fuel pump system 21 may include one or more pumps for pressurizing fuel delivered to the injectors of engine 110, such as the example injector 66 shown. While only a single injector 66 is shown, additional injectors are provided for each cylinder. It will be appreciated that fuel system 118 may be a return-less fuel system, a return fuel system, or various other types of fuel system.

An EGR system 24 may be present to divert a portion of the exhaust back to the intake via EGR passage 28. Control of flow through the EGR system 24 may be provided by EGR valve 22, herein positioned at the junction of the EGR passage 28 with the exhaust system. EGR reduces oxygen content in the intake, which may result in lowered peak combustion temperatures, improving emissions.

FIG. 2 also shows the particle sensor 100 arranged downstream of the emissions control device 70. The sensor 100 and device 70 are arranged in the exhaust system 101. The exhaust gas from the engine 110 may flow through the particle sensor 100 and out to another exhaust passage or to the atmosphere, as shown by the arrows in FIG. 2.

The vehicle system 60 may further include control system 114. Control system 114 is shown receiving information from a plurality of sensors 116 (various examples of which are described herein) and sending control signals to a plurality of actuators 81 (various examples of which are described herein). As one example, sensors 116 may include exhaust gas sensor 126 located upstream of the emission control device, particle sensor 100, temperature sensor 128, and pressure sensor 129. Other sensors such as pressure, temperature, air/fuel ratio, and composition sensors may be coupled to various locations in the vehicle system 60. As another example, the actuators may include fuel injector 66, valve 22, and throttle 62. The control system 114 may include a controller 112. The controller may receive input data from the various sensors, process the input data, and trigger the actuators in response to the processed input data based on instruction or code programmed therein corresponding to one or more routines. Example control routines are described herein with regard to FIG. 3.

Figure 3:
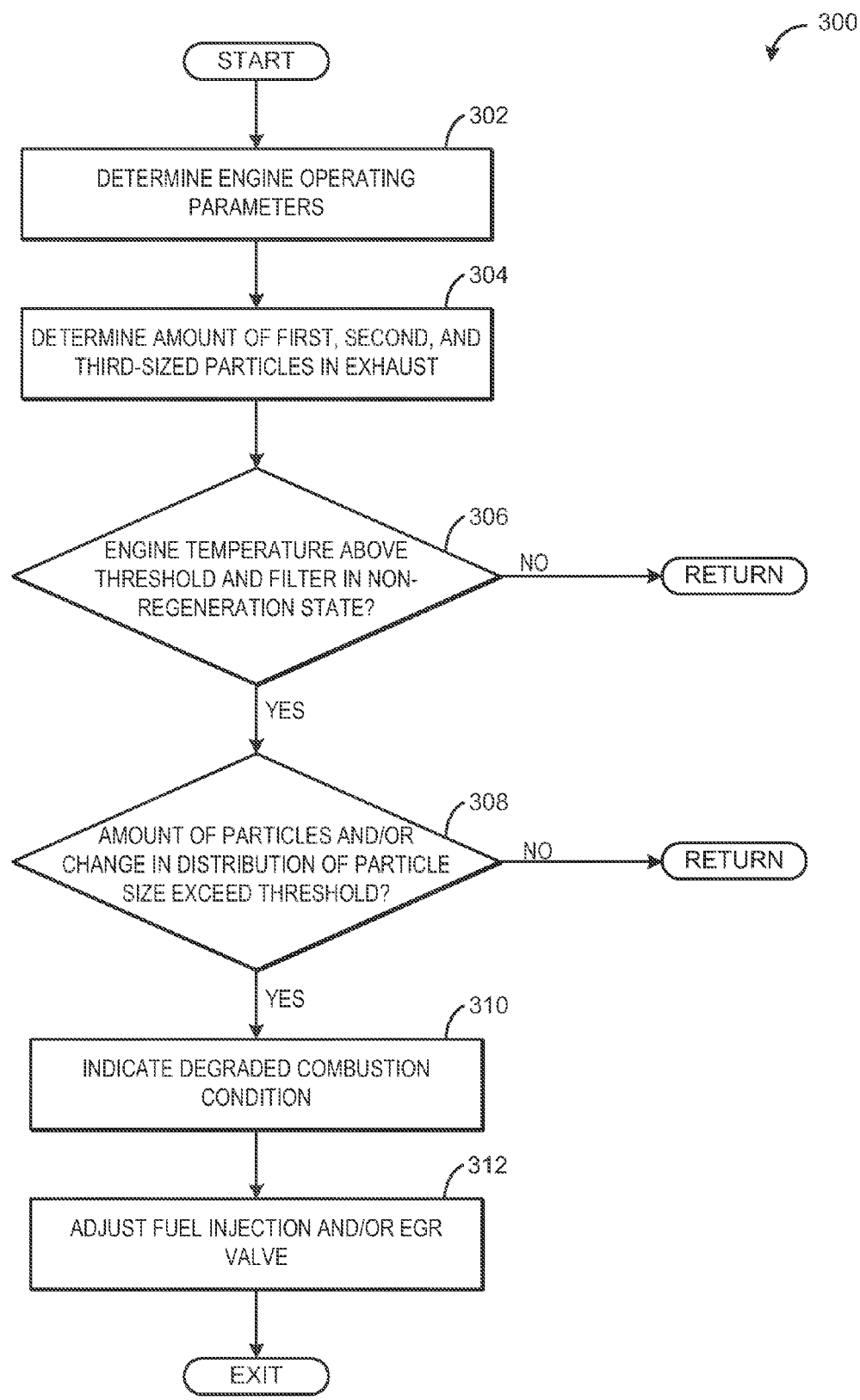
FIG. 3 is a flow chart illustrating an example method of controlling combustion stability according to an embodiment of the present disclosure.

FIG. 3 depicts a method 300 for maintaining combustion stability in an engine. Method 300 may be carried by a control system of a vehicle, such as controller 112, in response to feedback from one or more sensors, such as particle sensor 100. Method 300 includes, at 302, determining engine operating conditions. Engine operating conditions may include engine speed, load, temperature, etc. Engine operating conditions may also include fuel injection timing and amount, whether the EGR system is enabled, and whether any emissions control devices, such as particulate filters, are in a regeneration state. At 304, the amount of first-sized particles, second-sized particles, and third-sized particles in the exhaust are determined by the particle sensor. This may include routing exhaust through three inlets of the particle sensor. As explained above, each inlet of the particle sensor may be different sized such that only the first-sized particles may enter a first inlet, only first and second sized particles may enter a second inlet, and first, second and third sized particles may enter a third inlet. In this way, the amount of each sized particle in the exhaust may be determined.

At 306, it is determined if engine temperature is above a threshold and if the particulate filter is in a non-regeneration state. If one or both of these conditions is not met (e.g., the answer is no) method 300 returns. If the conditions are met, the particle size distribution based on feedback from the particle sensor may be used to monitor combustion stability.

As particles in the exhaust are a by-product of the combustion process, the amount and distribution of different sized particles in the exhaust may indicate altered or degraded combustion. In one example, if the portion of large particles in the exhaust increases, it may be indicative of misfire, pre-ignition, too-lean combustion, etc., which may result in increased emissions. To avoid and/or mitigate this, at 308, it is determined if the amount and/or distribution of the different sized particles in the exhaust has changed more than a threshold amount. A baseline amount and distribution of different sized particles in the exhaust may be determined based on sensor readings during stable combustion immediately following engine manufacture, for example, or based on a model determined off-line, or based on a rolling average of sensor readings during the current engine operation. If the amount or distribution of the particles deviates significantly from this baseline, it may indicate a degraded combustion condition, or degraded particulate filter condition.

The first, second, and third sized particles may be the smallest third of all particles, the intermediate third of all particles, and the largest third of all particles, respectively. However, the first, second, and third sized particles may be other suitable size classifications. For example, a change in the amount of very large-sized particles may be more indicative of degraded combustion than a change in the amount of other sized particles. In this case, the first sized particles may the smallest 80% of all sized particles, while the third sized particles may be the largest 10% of all sized particles, in order to more accurately monitor a change in the amount of the very large-sized particles.

In one example, a change in the distribution of different sized particles above a threshold may include a change in one or more sized particles of 10%, or 20%, or another suitable amount, of the total particles in the exhaust. In other example, the distribution may not change, but the amount of all the total particles may change.

If the amount and/or distribution of particles have not changed more than the threshold amount, method 300 returns. If the amount and/or distribution have changed by more than the threshold amount, a degraded combustion condition is indicated at 310. To mitigate this, at 312, fuel injection and/or an EGR valve may be adjusted to improve combustion stability. In one example, if the largest-sized particles increase by more than 10%, the EGR valve may be adjusted to lower the EGR percentage in the charge air, thus increasing the amount of oxygen to promote increased combustion stability. In another example, if the largest-sized particles increase by more than 10%, the EGR valve may be adjusted to increase the EGR percentage to lower peak combustion temperatures. Fuel injection may additionally or alternatively be adjusted. If the amount of the smallest-sized particles increases by more than 10%, for example, it may be desired to increase the amount of large-sized particles, as the large-sized particles may be better retained in the particulate filter than the small sized particles. To increase particle size, fuel may be injected later in some embodiments, or may be injected earlier in other embodiments.

Thus, method 300 provides for monitoring the distribution of two or more sized particles in the exhaust system of a vehicle. By monitoring a change in the amount and/or distribution of each sized particle, instability in combustion may be determined. In some embodiments, the monitoring of change in particle size may only be performed when engine temperature is above a threshold, such as 100° F., so that combustion conditions under standard, non-cold operation can be monitored. Further, the degraded combustion may not be indicated if the particulate filter is undergoing a regeneration, as the regeneration may result in changes in particulate size that are not indicative of combustion instability or a degraded combustion condition.

Thus, in one embodiment, FIG. 3 provides a method for maintaining combustion stability in an engine comprising monitoring a proportion of each of first, second, and third-sized particulate matter within an exhaust stream via a particle sensor, and during select conditions, adjusting fuel injection and/or an exhaust gas recirculation rate in response to a change in a distribution of the first, second, and third-sized particles exceeding a threshold. The method may also include monitoring the proportion of each of first, second and third-sized particulate matter within the exhaust stream via the particle sensor further comprises routing the exhaust stream through a small-sized inlet opening, a medium-sized inlet opening, and a large-sized inlet opening of the particle sensor, wherein each inlet opening is an inlet opening for a duct housing a sensing element. The select conditions comprise a particulate filter upstream of the particle sensor being in a non-regeneration state, and/or engine temperature being above a threshold.

FIG. 3 may also provide an engine method comprising adjusting engine operation in response to sizes of exhaust particulates. The method may also include that the adjusting includes adjusting fuel injection and exhaust gas recirculation in response to a change in a relative proportion of different sized exhaust particulates.

It will be appreciated that the configurations and methods disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A particle sensor for an exhaust system, comprising:
   a first inlet opening and a second inlet opening for receiving an exhaust-gas flow of the exhaust system, wherein the first inlet opening and the second inlet opening are of different sizes; and
   a first sensor element and a second sensor element, wherein the first sensor element is arranged downstream of the first inlet opening for detecting a first amount of particles flown through the first inlet opening, and the second sensor element is arranged downstream of the second inlet opening for detecting a second amount of particles flown through the second inlet opening.

2. The particle sensor as claimed in claim 1, wherein each of the first sensor element and the second sensor element has a resistance element.

3. The particle sensor as claimed in claim 1, wherein each of the first sensor element and the second sensor element is arranged in a duct which adjoins a respective inlet opening, wherein different sensor elements are arranged in different ducts.

4. The particle sensor as claimed in claim 1, wherein a size of at least one of the first inlet opening and the second inlet opening is variable.

5. The particle sensor as claimed in claim 1, wherein the first inlet opening is a smallest inlet opening, and wherein an integral mass of particles of a size smaller than or the same as the smallest inlet opening is a function of measurements by the first sensor element arranged downstream of the smallest inlet opening.

6. The particle sensor as claimed in claim 5, wherein the second inlet opening is a next-larger inlet opening than the smallest inlet opening, and wherein an integral mass of particles of a size smaller than or the same as the next-larger inlet opening is a function of measurements by the second sensor element arranged downstream of the next-larger inlet opening minus the function of measurements by the first sensor element arranged downstream of the smallest inlet opening.

7. A method for detecting particles in an exhaust gas of an internal combustion engine, comprising:
  flowing the exhaust gas through a particle filter with a first opening of a first opening size and a second opening of a second opening size, the first opening size different from the second opening size;
  measuring a first amount of the particles of a first particle size downstream of the first opening of a first size via a first sensor element; and
  measuring a second amount of the particles of a second particle size downstream of the second opening via a second sensor element, different from the first sensor element, wherein the second particle size is different from the first particle size.

8. The method as claimed in claim 7, wherein particles of sizes different from the first particle size and the second particle size are measured.

9. The method as claimed in claim 7, wherein the particles are measured by a resistance element of each of the first sensor element and the second sensor element.

10. The method as claimed in claim 7, further comprising flowing particles through additional openings of the particle filter, and wherein a number of the additional openings, the first opening size, the second opening size, and opening sizes of the additional openings are determined by a soot distribution in the exhaust gas.

11. The method as claimed in claim 7, wherein at least one of the first opening size and the second opening size can be varied.

12. The method as claimed in claim 11, wherein the at least one of the first opening size and the second opening size is varied based on particle size.

13. The method as claimed in claim 11, wherein the at least one of the first opening size and the second opening size is varied conjunction with a cleaning of a sensor element arranged downstream of each of the openings.

* * * * *

UNITED STATES PATENT AND TRADEMARK OFFICE
CERTIFICATE OF CORRECTION

PATENT NO. : 9,874,509 B2
APPLICATION NO. : 14/724049
DATED : January 23, 2018
INVENTOR(S) : Yasser Mohamed Sayed Yacoub et al.

Page 1 of 1

It is certified that error appears in the above-identified patent and that said Letters Patent is hereby corrected as shown below:

In the Claims

Column 10, Line 2, Claim 7, delete "of a first size" immediately after "size downstream of the first opening".

Signed and Sealed this
Tenth Day of July, 2018

Andrei Iancu
*Director of the United States Patent and Trademark Office*